(12) United States Patent
Edme et al.

(10) Patent No.: US 8,551,031 B2
(45) Date of Patent: Oct. 8, 2013

(54) SWAB APPLICATOR AND METHODS OF USE

(76) Inventors: Colson Edme, Brooklyn, NY (US);
Ginette Aubin-Edme, Brooklyn, NY (US)

( * ) Notice: Subject to any disclaimer, the term of this patent is extended or adjusted under 35 U.S.C. 154(b) by 304 days.

(21) Appl. No.: 13/099,989

(22) Filed: May 3, 2011

(65) Prior Publication Data
US 2012/0283616 A1 Nov. 8, 2012

(51) Int. Cl.
*A61F 13/38* (2006.01)

(52) U.S. Cl.
USPC .............................................. 604/1

(58) Field of Classification Search
USPC ........................................ 604/1–3
See application file for complete search history.

(56) References Cited

U.S. PATENT DOCUMENTS

| | | | |
|---|---|---|---|
| 4,953,560 A * | 9/1990 | Samuels ................... | 600/572 |
| 5,067,194 A * | 11/1991 | Rosenfeld et al. ........... | 15/144.2 |
| 5,158,532 A | 10/1992 | Peng et al. | |
| 5,183,461 A * | 2/1993 | Hobbs ..................... | 604/540 |
| 5,715,559 A * | 2/1998 | Mitri ...................... | 15/118 |
| 5,738,643 A * | 4/1998 | Stredic, III .............. | 604/1 |
| 5,766,143 A | 6/1998 | Bennett | |
| 5,902,262 A | 5/1999 | Bastioli et al. | |
| 6,623,440 B1 * | 9/2003 | Weldon ................... | 604/1 |
| 6,695,802 B1 * | 2/2004 | Thompson ............... | 604/1 |
| 6,957,958 B2 * | 10/2005 | Rowe et al. .............. | 433/89 |
| 7,074,230 B2 | 7/2006 | Olson | |
| 7,211,061 B1 * | 5/2007 | Maxwell ................... | 604/1 |
| 7,563,239 B1 | 7/2009 | Hudson et al. | |
| 2001/0025155 A1 * | 9/2001 | Yoon ....................... | 604/1 |
| 2003/0108846 A1 * | 6/2003 | Hoertsch .................. | 433/216 |
| 2003/0181840 A1 * | 9/2003 | Tsaur ....................... | 604/1 |
| 2004/0220506 A1 | 11/2004 | Gordon et al. | |
| 2004/0267180 A1 * | 12/2004 | Beaudry ................... | 604/1 |
| 2005/0171462 A1 * | 8/2005 | Tsaur ....................... | 604/1 |
| 2007/0049860 A1 * | 3/2007 | Seminara ................. | 604/1 |
| 2007/0167900 A1 * | 7/2007 | Kanjilal et al. .......... | 604/1 |
| 2007/0299457 A1 * | 12/2007 | Morales ................... | 606/162 |
| 2008/0119776 A1 * | 5/2008 | Wu ........................... | 604/1 |
| 2008/0142385 A1 * | 6/2008 | Stein et al. ............... | 206/362 |
| 2008/0208100 A1 | 8/2008 | Wolff | |
| 2009/0062715 A1 * | 3/2009 | Saunders et al. ......... | 604/1 |
| 2009/0300867 A1 | 12/2009 | Farhoudi | |
| 2011/0054377 A1 * | 3/2011 | Lafe ........................ | 604/1 |
| 2011/0087133 A1 * | 4/2011 | Ching et al. ............. | 600/572 |
| 2011/0155043 A1 * | 6/2011 | Haarer et al. ............ | 116/201 |

* cited by examiner

*Primary Examiner* — Susan Su
(74) *Attorney, Agent, or Firm* — Cowan, Liebowitz & Latman, P.C.; Mark Montague; Serge Krimnus

(57) ABSTRACT

A swab applicator for collecting debris and other materials from small and hard to reach spaces and cavities and applying materials to selected areas, including small and hard to reach spaces and cavities. The swab applicator includes an elongated member having two opposite ends having respective end members extending from the ends. One of the end members loops to form one or more through openings and has a surface made from or covered with an absorbent material. The other end member is different from the first end member and, in one configuration, is a wad mounted on the end of the elongated member.

16 Claims, 4 Drawing Sheets ly detail below, the present invention
SWAB APPLICATOR AND METHODS OF USE

FIELD OF THE INVENTION

The present invention relates to devices for collecting and applying various materials and substances from and to selected areas. More particularly, the present invention relates to swab applicators for cleaning orifices and other cavities, small and/or hard to reach spaces and applying substances to selected areas, and methods for their use.

BACKGROUND OF THE INVENTION

Cotton swabs can be found in almost every household and are used in numerous applications. For example, cotton swabs are used to collect samples of microbiological cultures, DNA, and other substances by swiping an area of interest. Cotton swabs are also used in surgical procedures and/or to apply a medication, cleaning solution, ointment, and/or other substances to a selected area. Some users apply and/or remove make-up or other cosmetic formulas with cotton swabs. Other users clean small and/or tight spaces, such as a laser head of a CD/DVD player, with cotton swabs. However, the most common use of the cotton swabs is to remove cerumen (dead skin and secretions) and other ear debris from external ear canals and lobes.

A typical cotton swab includes a plastic stem having both ends wrapped with a cotton wad. By inserting one of the ends into the external ear canal and rotating the end inside the ear canal, the user is able to remove some of the cerumen collected within the ear canal. However, the ear canals have multiple cavities that collect cerumen, which makes it harder for the user to dislodge the cerumen. The typical cotton swab is not well suited for such a task and requires a lot of effort by the user to dislodge the cerumen. Further, while attempting to dislodge the cerumen, the user of the typical cotton swab may have to flatten the cerumen before removing it and/or inadvertently push the cerumen deeper into the ear canal, instead of removing the cerumen. Flattening of the cerumen and pushing of the cerumen inside the ear canal is unhealthy and may cause ear drum damage, bacterial infection, and other health complications.

U.S. Pat. No. 5,766,143 discloses a cotton swab, whose end includes a conical member covered by cotton absorbent covering. Use of the conical member assures that the cotton swab's end has a size that is sufficiently large to prevent the user from inserting the cotton swab too deeply into the ear canal. U.S. Pat. No. 5,158,532 discloses an applicator swab having a swab head mounted on a support member with accordion-like folds located beneath the swab head. The accordion-like folds limit the pressure that can be exerted by the swab against the surface upon which the swab is being pushed. U.S. Publication No. 2008/0208100 describes an applicator swab having a swab tip, the surface of which is covered with a medical grade pressure sensitive adhesive. The adhesive for covering the surface of the swab tip is selected with such characteristics as to provide sufficient tack force to attach to and dislodge a large piece of cerumen from a person's ear. U.S. Pat. No. 7,563,239 discloses a cotton swab having a tapered end made from cotton and covered by a layer of exfoliating material, such as a loofah sponge.

U.S. Publication No. 2004/0220506 discloses a swab having each of the ends wrapped in terry cloth fabric that is affixed to the ends using an adhesive that prevents unraveling of the cloth. U.S. Publication No. 2009/0300867 discloses a cleaning swab having a handle with a thickened portion, which includes an internal canal forming a recess near the end of the thickened portion for collecting earwax when the user scraps the surface of the inner ear with the thickened portion. The handle of the cleaning swab may also include a stop surface, such as a disk, to prevent insertion by the user of the cleaning swab too deeply into the ear canal. U.S. Pat. No. 7,074,230 discloses an ear-cleaning device having a plastic body with an integral scoop at the end. The scoop has openings formed in the bottom of its bowl for scraping wax from the ears.

However, there is still a need for a cleaning device that allows for efficient removal of cerumen and minimizes the chance of a user damaging the ear canal or ear drum when using the cleaning device.

SUMMARY OF THE INVENTION

As set out in further detail below, the present invention entails, in accordance with one embodiment, a swab applicator that comprises an elongated member having two ends and two different end members attached respectively to the ends of the elongated body. In one embodiment, a first end member loops to form one or more through openings and is configured to enable dislodging and removal of debris (such as a cerumen) from a cavity, indentation, or a hard to reach space (such as an ear canal). When the first end member is inserted into the cavity, placed such as to capture a piece of debris in one of the through openings of the first end member, and removed from the cavity, the captured piece of debris is removed from the cavity along with the first end member. In one embodiment, the first end member also comprises a covering layer including an adhesive that enables capturing of debris coming into proximity with the covering layer.

The shape of the first end member of the swab applicator varies between different embodiments, e.g., a hook, a letter of an alphabet, a two-dimensional ovoid, a spheroid, a triangle, a rectangle, a tear-drop, and the like. Further, the first end member of the swab applicator may be rigid or flexible. In some embodiments, the first end member is substantially flat. In one embodiment, the first end member of the swab applicator comprises a three-dimensional ovoid portion having a plurality of through openings formed by looping of the first end member, where the ovoid portion defines a chamber inside the first end member and is configured to enable dislodging and removal of a piece of debris from a cavity. When the first end member is inserted into the cavity, placed over the piece of debris such that the piece of debris is located within one of the through openings, and moved (e.g., rotated), the piece of debris becomes dislodged and captured within the chamber.

In another embodiment, the first end member comprising a three-dimensional ovoid shaped full portion having a surface with one or more indentations formed therein, where the full portion is configured to enable dislodging and removal of a piece of debris from a cavity. When the first end member is inserted into the cavity, placed over the piece of debris such that the piece of debris is within one of the indentations of the full portion, and then moved (e.g., rotated, moved back and forth), the piece of debris becomes dislodged and trapped within the indentation. The indentations of the full portion may be formed in its surface in one or more directions, including longitudinally to the elongated member of the swab applicator, substantially perpendicular to the elongated member of the swab applicator, at an angle to the longitude of the elongated member, and the like. Further, an absorbent covering layer may be attached to the surface of the full portion. In one embodiment, the covering layer replicates the indentations in the surface of the full portion. In another embodiment, the indentations are formed directly in the covering layer.

In one embodiment, the swab applicator of the present invention is configured to enable dislodging and removal of pieces cerumen of different sizes, where the first end member (e.g., an end member having one or more through openings) is used for removal of larger pieces of cerumen, while the second end member (e.g., a cotton wad mounted on the respective end of the elongated member) is used for removal of smaller pieces of cerumen. Further yet, in some embodiments, the first and/or second end members are integral components of the swab applicator extending from the respective ends of the elongated member, while in some other embodiments, one or both end members are securely mounted on the elongated member. Also, in some embodiments, all of the components of the swab applicator are entirely biodegradable. Paper, biodegradable plastic, wood, polyester, rayon fiber, polyurethane, cotton fiber, resin, natural rubber, medical grade adhesive, and mixtures thereof are some of the materials that may be used to make the components of the entirely biodegradable swab applicator.

One embodiment of the present invention provides a method for cleaning a cavity. The method comprises providing a swab applicator that includes an elongated member having first and second ends with respective first and second end members attached thereto, where the first end member loops to form one or more through openings and includes a covering layer and where the second end member includes a wad securely mounted on the second end of the elongated member. The method further comprises inserting one of the first and second end members into the cavity and using the inserted end member to remove a piece of debris. If the first end member is used to remove the piece of debris, the using step includes placing the first end member over the piece of debris such as to capture the piece of debris within one of the through openings of the first member and removing the first end member from the cavity to remove the captured piece of debris. If the second end member is used to remove the piece of debris, the using step includes rotating the second end member within the cavity to dislodge and capture the piece of debris and removing the second end member from the cavity to remove the captured piece of debris.

Various other objects, advantages and features of the present invention will become readily apparent to those of ordinary skill in the art from the following detailed description of the invention.

BRIEF DESCRIPTION OF THE DRAWINGS

The following detailed description, given by way of example and not intended to limit the present invention solely thereto, will best be appreciated in conjunction with the accompanying drawings, wherein like reference numerals denote like elements and parts, in which.

DETAILED DESCRIPTION OF THE PRESENT INVENTION

The present invention pertains to various embodiments of a swab applicator having unique shape(s) for collecting and applying various materials and substances from and to small and/or hard to reach cavities and other spaces. As described below in greater detail, some embodiments of the present invention provide a swab applicator for more efficient collection and removal of cerumen and other debris from an ear canal. The swab applicator includes an elongated body (member) with two ends and two end members attached to the respective ends of the body. In accordance with some embodiments, at least one of the end members is looped to form one or more openings facilitating collection of the cerumen and other debris from the ear canal and has its surface covered with absorbing materials. The shape of the looped member and a number of formed openings varies between different embodiments. In some embodiments, the second end member differs from the first end member. Also, in accordance with some embodiments, the entire swab applicator is made from biodegradable materials, such as paper, biodegradable plastic, wood, bamboo, wire, polyester, rayon fibers, cotton fibers, polyurethane, and the like.

Figure 1:
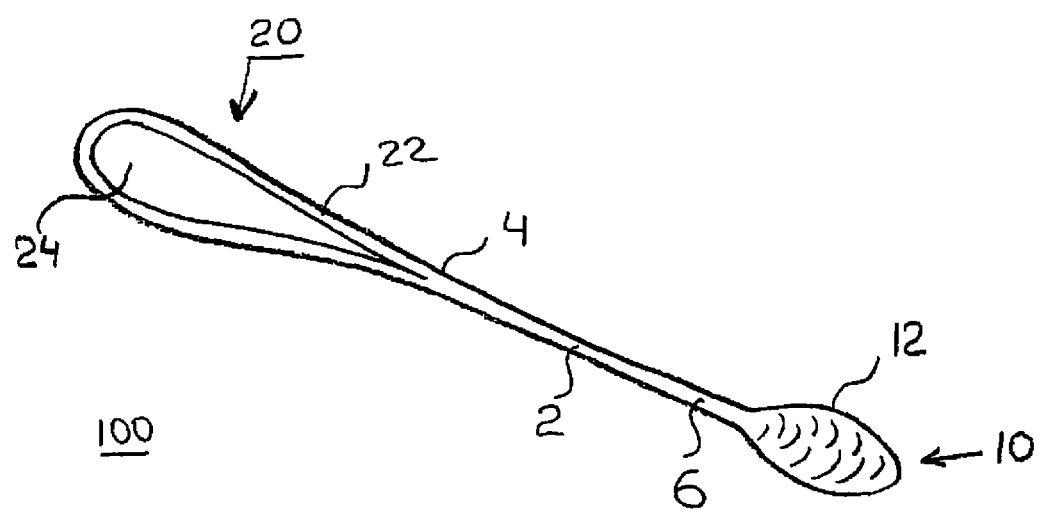
FIG. 1 is a schematic illustration of a swab applicator in accordance with one embodiment of the present invention.
Figure 2:
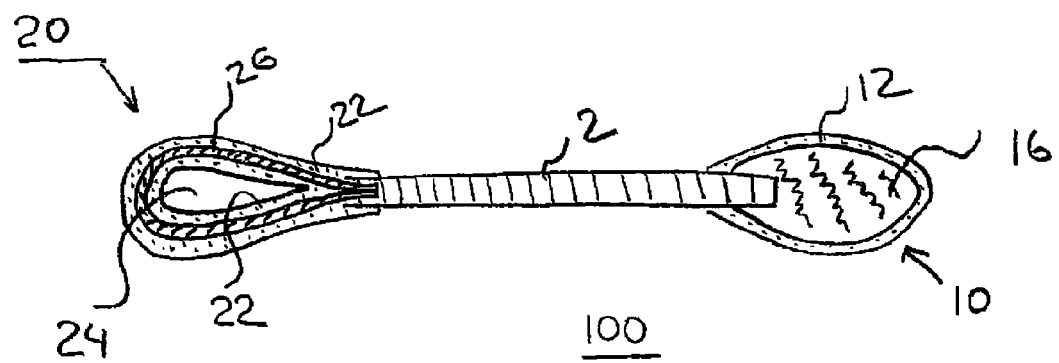
FIG. 2 is a cross-section view of the swab applicator shown in FIG. 1.

Referring to the figures and specifically to FIGS. 1 and 2 thereof, there is shown a swab applicator 100 in accordance with one embodiment of the present invention. The swab applicator 100 includes three primary components—an elongated body 2 (member, stem, etc.) and two end members 10 and 20 extending on the opposite sides (ends) of the body 2. The body 2 of the swab applicator 100 serves as a holder of the two end members 10 and 20 and includes holder portions 4 and 6 for holding the swab applicator when the end member 20 or the end member 10 is respectively used. Generally, the body 2 is a rod or a tube made from plastic, rolled paper, wood, or other suitable material. In some embodiments, the body 2 has a different profile, such as a prism (triangular, rectangular, pentagonal, etc.) and/or shape, such as curvy, zigzag, wavy, etc. Also, the body 2 may be hollow or solid.

Although not shown, the holder portion 4 and/or holder portion 6 may be configured differently from the body 2 so as to provide for a more convenient and secure grip of the swab applicator 100. For example, in some embodiments, the holder portion 4 and/or 6 has a wider diameter than the body 2 and/or a different surface than the rest of the body 2 (e.g., bumps, indentations, etc.). In some other embodiments, the holder portion 4 and/or 6 is also shaped differently from the rest of the body 2, e.g., is curvy or flat as compared to the rest of the body.

In the illustrative embodiment of FIGS. 1 and 2, the end member 20 includes a main portion 26, which loops to form a through opening 24 for facilitating capturing of debris from inside of orifices and other cavities and other hard to reach spaces. In some embodiments, the main portion 26 of the end member 20 is made from a suitable flexible material that tends to retain its shape (e.g., certain types of plastic). The flexible end member 20 facilitates use of the swab applicator when it is being inserted in tight spaces and/or curved cavities by enabling the end member 20 to change its shape. In some other embodiments, the main portion 26 of end member 20 is made from a suitable rigid material (e.g., wood). The end member 20 could also be made from plastic, wood, bamboo, rolled paper, wire, and other suitable materials.

As further shown in FIGS. 1 and 2, the end member 20 may also include a covering layer 22 that forms or covers the surface of the end member 20. The covering layer 22 may be incorporated in the surface of the end member 20 or attached to the surface of the end member 20 by dipping, coating, sputtering, wrapping, winding, molding, threading, knotting, weaving, or any other suitable process. In some embodiments, the covering layer 22 is made from a suitable soft absorbent material and covers the entire surface of the end member 20. Examples of the soft absorbent material used to make the covering layer 22 include, but are not limited to, polyester, rayon, and cotton fibers or mixtures thereof, polyurethane, and the like. The covering layer 22 may further include a medical grade adhesive capable of capturing and holding cerumen, dust, or other debris.

Means of attaching or securing the end member 20 to the body 2 varies between different embodiments of the present invention. For example, as shown in FIG. 2, the main portion 26 may be partially inserted into an opening of the respective end of the body 2 and secured in such a state using an adhesive, friction force, etc. Additionally, or in the alternative, the covering layer 22 may be used to secure the end member 20 on the body 2. However, in some embodiments, the main portion 26 of the end 20 is made from the same material as the body 2 and is an integral part (extension) of the body 2.

The end member 10 of the swab applicator 100 is mounted on the respective end of the body 2 and includes a main ovoid-shaped portion 16, such as a wad wrapped around the end of the body 2, as shown in FIG. 2. In some embodiments, the ovoid-shaped portion 16 is inserted into an opening in the respective end of the body 2, instead of being wrapped around or attached by an adhesive. Further, in some embodiments, the end member 10 includes an additional covering layer 12 made from an absorbent material such as medical grade adhesive. Polyester, rayon, and cotton fibers or mixtures thereof, polyurethane, and like materials may also be used. In some other embodiments, only main portion 16 is used, without the covering layer 12.

As shown in FIG. 1, the end members 10 and 20 of the swab applicator 100 differ from each other. Further, the covering layers 12 and 22 of the end members 10 and 20 respectively may also be made from different materials. Using different materials and covering materials to make the end members 10 and 20 enables the swab applicator 100 to provide a user with flexibility and convenience in using the swab applicator, where a user's specific needs define which particular end member the user would use. For example, in the illustrative embodiment of FIG. 1, the user may elect to use the circular end member 20 to remove larger, dryer, and stickier pieces of cerumen by placing the end member 20 above the piece of cerumen and pulling it out of the ear canal. However, if the user intends, for example, to absorb moisture from the ear canal, such as after shower or swimming, or remove a smaller piece of cerumen, the end member 10 may be selected instead.

Figure 3:
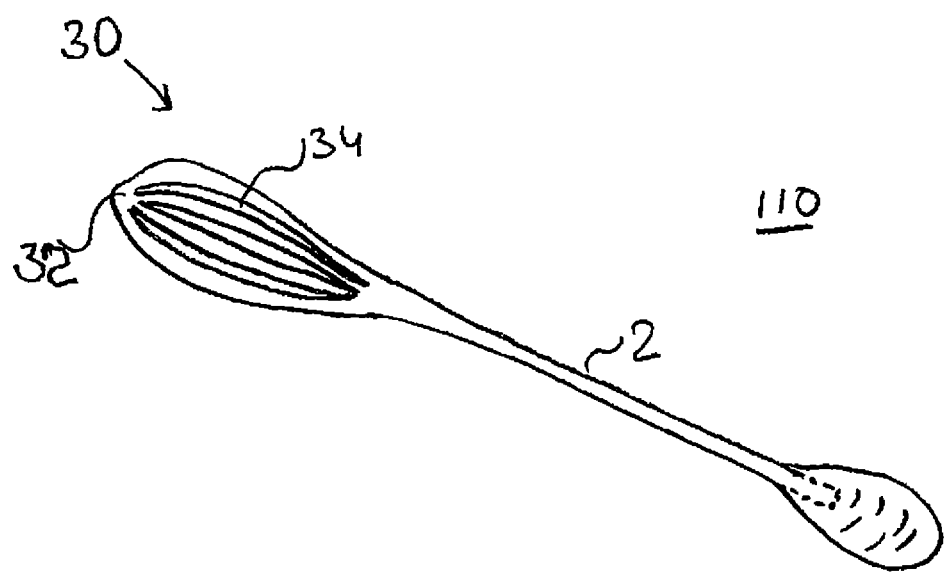
FIG. 3 is a schematic illustration of a swab applicator in accordance with another embodiment of the present invention.

Turning now to FIG. 3 of the drawings, FIG. 3 shows a schematic illustration of a swab applicator 110 in accordance with another embodiment of the present invention. In particular, the swab applicator 110 of this embodiment, similar to the above-described embodiments, includes three main components—an elongated body 2 and two end members 10 and 30 extending from the opposite sides of the body 2. As shown in FIG. 3, the end member 10 is substantially similar to the end member 10 shown in FIGS. 1 and 2 that is discussed above. However, the end member 30, differs from the end members 10 and 20 discussed above.

Specifically, in the illustrative embodiment of FIG. 3, the end member 30 has a three-dimensional ovoid shape with multiple indentations (cavities) 34 formed in the surface 32 to facilitate capturing of cerumen and other debris. When the user inserts the swab applicator 110 using the end member 30 into a cavity, such as an ear canal, and swipes the swab applicator 110 along a surface of the cavity, pieces of debris, such as pieces of cerumen become dislodged by and/or trapped within the indentations 34, and thus can be easily removed from the cavity.

The indentations 34 shown in FIG. 3 have elongated, crescent-like shapes and are formed in the surface 32 in a direction longitudinal to the body 2. However, in accordance with the present invention, the indentations 34 may have a different shape and size and/or be formed in a different manner. For example, in some embodiments, the indentations 34 are formed in a direction substantially perpendicular to the body 2, at multiple angles to the longitude of the body 2, and the like. Other examples of variations in the indentations 34 as between different end members 30 or within a single end member 30 include, but are not limited to, using different shapes (e.g., circular, parabolic, etc.), depth (e.g., shallow, deep), length (e.g., short and long), and the like. The indentation 34 may also be formed in the surface 32 to fully circle the end member 30, spiral around the end member 30, and so on.

In accordance with embodiments of the present invention, various materials could be used to make the end member 30, for example, plastic, wood, bamboo, wire, rolled paper, and other suitable materials. The end member 30 may be formed using the same material as the material of the body 2 or a different material. In some embodiments, the end member 30 is the integral part of the body 2 and extends from the body 2. In some other embodiments, the end member 30 is attached to the body 2 using, for example an adhesive, friction force, and so on. Further, in some embodiments, the surface 32 of the end member 30 is covered with an absorbent soft material in the manner similar to the described above with respect to FIGS. 1 and 2. The absorbent soft material is attached to the surface 32 such as to keep the shape profile of the indentations 34. In some other embodiments, the indentations 34 are formed only within the layer of the absorbent material instead of surface 32 of the end member 30.

Figure 4A:
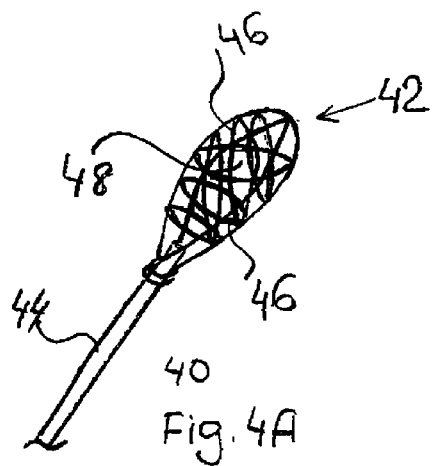
FIGS. 4A-4F are schematic illustrations of an end portion of a swab applicator in accordance with various embodiments of the present invention.

Referring now to FIGS. 4A-4F of the drawings, these figures show various embodiments of an end portion of a swab applicator in accordance with the present invention. In particular, FIG. 4A shows an end portion 40 of a swab applicator that includes an end member 42 mounted on or extending from a body 44 of the swab applicator. The end member 42 has a three-dimensional ovoid shape which is formed by looping a main component 46 (e.g., wire, plastic, and other suitable materials) of the end member 42. The looping of the main component 46 creates multiple through openings 48 within the end member 42 for capturing cerumen and other debris. In some embodiments, the main component 46 is looped such as to define a three-dimensional shape of the end member 42 having empty space (chamber) inside the chamber of the end member 42. In some other embodiments, the main component 46 is also looped through the inner space of the end member 42.

In some embodiments, the surface of the main component 46 of the end member 42 is covered with a layer of absorbent soft material in the manner similar to the description above with respect to FIGS. 1 and 2. The covering layer may include adhesive components to facilitate trapping of debris on and/or inside the end member 42. When the user inserts the end member 42 into a cavity, such as an ear canal, and swipes or rotates the end member 42 along the surface of the cavity, pieces of debris, such as pieces of cerumen become trapped within the end member 42 through the openings 48, and thus could be easily and safely removed from the cavity.

Figure 4B:
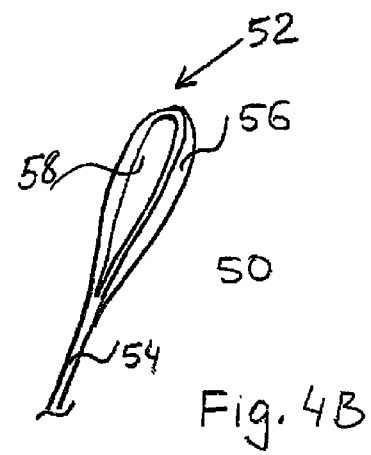

FIG. 4B shows an end portion 50 of a swab applicator in accordance with another embodiment of the present invention. The end portion 50 includes an end member 52 mounted on or extending from a body 54 of the swab applicator. The end member 52 has a three-dimensional scoop-like shaped body 56, which forms an opening 58 that enables dislodging and capturing of debris inside the scoop of the body 54. In some embodiments, the outside and/or inner surfaces of the body 56 are covered with an absorbent soft material in the manner similar to the described above with respect to FIGS. 1 and 2. By inserting the end member 52 into a cavity, such as an ear canal, and placing the opening 58 above cerumen or other debris, the user may easily and safely capture and remove the cerumen and other debris from the cavity.

Figure 4C:
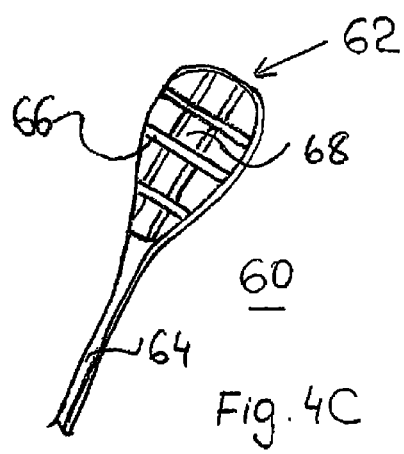

FIG. 4C shows an end portion 60 of a swab applicator that includes an end member 62 mounted on or extending from a body 64 of the swab applicator, in accordance with one embodiment of the present invention. The end member 62 includes a main component having a two-dimensional ovoid shape defining multiple openings 68 within the end member 62 for facilitating removal of cerumen and other debris. In the illustrative embodiment of FIG. 4C, the main component is substantially flat. Although FIG. 4C shows that the main component 66 defines a grid pattern of openings 68, other patterns may be used (e.g., diagonal, dot, random, etc.). In some embodiments, the surface of the main component 66 of the end member 62 is covered with an absorbent soft material in the manner similar to the described above with respect to FIGS. 1 and 2. By inserting the end member 62 into a cavity, such as an ear canal, and placing one of the openings 68 above cerumen or other debris, the user may easily and safely dislodge and remove the cerumen and other debris from the cavity.

Figure 4D:
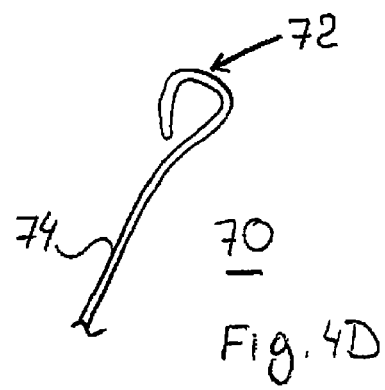
Figure 4E:
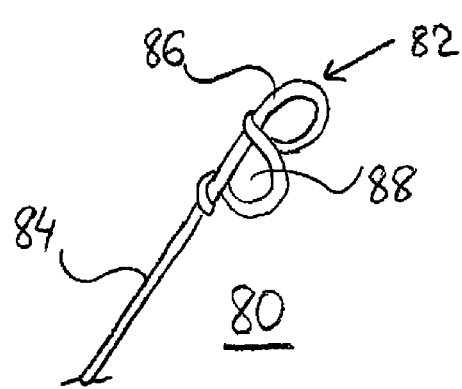
Figure 4F:
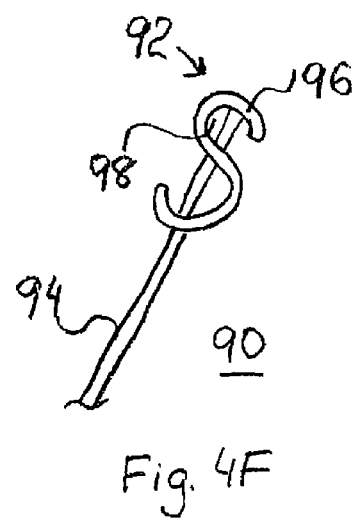

FIGS. 4D-4F show additional embodiments of an end portion of a swab applicator. In particular, in these illustrative embodiments, the end portion has a shape of a hook (FIG. 4D: 70) or a shape of an alphabet letter, such as "B" and "S" (FIG. 4E-4F: 80 and 90). Hooks and openings formed by the end members 72, 82, and 92 facilitate the removal of cerumen and other debris from various cavities by enabling the user to dislodge and/or capture the debris. Note that the present invention is not limited to the specific designs shown in FIGS. 4D-4F (or the other figures herein), but rather other designs may also be employed. For example, in accordance with the present invention, the end member may have a shape of another letter of alphabet (e.g. "Z").

As discussed above, in some embodiments, the end member of the swab applicator is mounted on the body of the swab applicator, for example, as shown in FIG. 4F where the end member 92 mounted to an end portion of the body 94 of the swab applicator. In some other embodiments, the end member of the swab applicator is the integral part of the swab applicator's body, for example, as shown in FIGS. 4D and 4E. Further, the entire surface or, alternatively, only a part of the surface of the end members could be covered with an absorbent soft material. Also, in some embodiments, one of both of the end members of the swab applicator are made from a suitable flexible material that tends to retain its original shape (e.g., certain types of plastic) after being flexed. Flexibility of the end member facilitates use of the swab applicator while it is being inserted in tight spaces and/or curved cavities by enabling the end member to change its shape. In some other embodiments, the end member is made from a suitable rigid material (e.g., wood).

In accordance with some embodiments, all of the components, including the covering layers, are made from environment-friendly materials, such as biodegradable materials. Examples of biodegradable materials that could be used in accordance with embodiments of the present invention include, but are not limited to, paper, biodegradable plastic, wood, bamboo, wire, polyester, rayon fibers, cotton fibers, polyurethane, resins, and natural rubbers.

Further, the present invention is not limited to the specific combinations of the end members shown in FIGS. 1-3. For example, other combinations of the end members could be used in a single swab applicator in accordance with the present invention (e.g., a combination of the end member 42 shown in FIG. 4A and the end member 92 shown in FIG. 4F). In addition, the present invention is not limited to any particular size or any particular color. Rather, in some embodiments, an intended user and/or use defines a particular design and size of the swab applicator. For example, a swab applicator for cleaning a child's ear would generally have a smaller size than a swab applicator for cleaning an adult's ear. If a swab applicator is to be used in a surgical procedure, a body and/or end member of different sizes could be used (e.g., longer, shorter, wider, narrower, etc.). Also, the shape of the end members of the swab applicator varies between different embodiments. Examples of the shapes that end member have include, but are not limited to, are ovoid, spheroid, triangle, rectangle, letter, tear drop, and the like. For example, a swab applicator having one or both end members shaped as a letter of alphabet in bright colors makes use of such swab applicators more appealing to children.

Also, in some embodiments the end members of the swab applicator differ such as to provide the user of the swab applicator with a greater flexibility in executing a particular task. For example, as described above, an end member having through openings or a surface with cavities is better suited to remove larger pieces of cerumen, while an end member having a full portion with a soft and/or absorbent covering is more suitable to remove moisture or smaller pieces of cerumen. Accordingly, a swab applicator which includes both such end members allows the user to be more flexible and efficient in cleaning an ear canal and/or lobe. In particular, the user may select the end member having through openings first to clean the larger pieces of cerumen, and then select the end member having the full portion to absorb moisture and remove smaller pieces of cerumen.

Further, one embodiment of the present invention provides a method for cleaning a cavity. The method includes providing a swab applicator that includes an elongated member having first and second ends with respective first and second end members attached thereto, where the first end member loops to form one or more through openings and includes a covering layer and where the second end member includes a wad securely mounted on the second end of the elongated member. The method further includes inserting one of the first and second end members into the cavity and using the inserted end member to remove a piece of debris. If the first end member is used to remove the piece of debris, the using step includes placing the first end member over the piece of debris such as to capture the piece of debris within one of the through openings of the first member and removing the first end member from the cavity to remove the captured piece of debris. If the second end member is used to remove the piece of debris, the using step includes rotating the second end member within the cavity to dislodge and capture the piece of debris and removing the second end member from the cavity to remove the captured piece of debris.

Although the description above focuses on cleaning of cavities, and ear canals in particular, it should be understood that cleaning an ear canal using the swab applicator is merely an illustrative example and not intended to limit the present invention solely thereto. In accordance with some embodiments, the swab applicator is used to apply substances to a selected area, e.g., ointment, make-up, paint, gel, and the like. As discussed above, in some embodiments, an intended use of the swab applicator defines a particular shape, size, and type of end members used in the swab applicator.

Having described the present invention including various features and variations thereof, it is intended that the appended claims be interpreted as including the embodiments described herein, the alternatives mentioned above, and all equivalents thereto.

What is claimed is:

1. A swab applicator, comprising:
an elongated member having first and second ends;
a first end member attached to the first end of the elongated member and having a covering layer; and
a second end member attached to the second end of the elongated member, the second end member being different from the first end member,
wherein the first end member comprises a three-dimensional ovoid portion having a plurality of through openings formed by loops, the ovoid portion defining a chamber.

2. The swab applicator of claim 1, wherein the first end member is configured to dislodge cerumen located in an ear canal when the first end member is inserted into the ear canal, placed over a piece of the cerumen to capture the piece of cerumen within one of the through openings of the first member, and moved after capturing the piece of cerumen.

3. The swab applicator of claim 2, wherein the first end member is further configured to enable removal of the cerumen from the ear canal when the first end member is removed from the ear canal along with the piece of cerumen captured in the one of the through openings of the first member.

4. The swab applicator of claim 1, wherein the second end member comprises a wad securely mounted on the second end of the elongated member.

5. The swab applicator of claim 1, wherein the three dimensional ovoid portion of the first end member is configured to enable dislodging of a piece of debris from a cavity using at least one of the plurality of through openings and capturing of the dislodged piece of debris within the chamber.

6. The swab applicator of claim 1, wherein the first end member is shaped as a tear drop.

7. The swab applicator of claim 1, wherein the covering layer comprises an adhesive, the covering layer adapted to enable capturing of debris that comes in proximity with the covering layer.

8. The swab applicator of claim 1, wherein the first end member is one of flexible and rigid.

9. The swab applicator of claim 1, wherein each component of the swab applicator is entirely biodegradable.

10. The swab applicator of claim 9, wherein each of the elongated member, the first end member, and the second end member is made from one or more of: paper, biodegradable plastic, wood, polyester, rayon fiber, polyurethane, cotton fiber, resin, natural rubber, medical grade adhesive, and mixture thereof.

11. The swab applicator of claim 1, wherein the first end member is one of an integral component of the elongated member that extends from the first end and a component that is securely mounted on the elongated member.

12. The swab applicator of claim 1, wherein
the first end member is configured to enable removal of a first piece of cerumen from an ear canal,
the second end member is configured to enable removal of a second piece of cerumen from the ear canal, and
the first piece of cerumen is larger than the second piece of cerumen.

13. The swab applicator of claim 1, wherein each of the elongated member, the first end member, and the second end member is made from one or more of: paper, biodegradable plastic, wood, bamboo, wire, polyester, rayon fibers, cotton fibers, polyurethane, resins, and natural rubbers, and
wherein the covering layer comprises one or more of rayon fiber, cotton fiber, polyester fiber, medical grade adhesive, and mixture thereof.

14. A method for cleaning a cavity, the method comprising:
providing a swab applicator comprising:
an elongated member having first and second ends,
a first end member attached to the first end of the elongated member, the first end member looping to form one or more through openings, the first end member having a covering layer, wherein the first end member comprises a three-dimensional ovoid portion having a plurality of through openings formed by loops, the ovoid portion defining a chamber, and
a second end member comprising a wad securely mounted on the second end of the elongated member;
inserting one of the first and second end members into the cavity; and
using the inserted end member to remove a piece of debris from the cavity, wherein:
if the first end member is used to remove the piece of debris, the using step comprises:
placing the first end member over the piece of debris such as to capture the piece of debris within one of the through openings of the first member, and
removing the first end member from the cavity to remove the captured piece of debris; and
if the second end member is used to remove the piece of debris, the using step comprises:
rotating the second end member within the cavity to dislodge and capture the piece of debris, and
removing the second end member from the cavity to remove the captured piece of debris.

15. The method of claim 14, wherein the first end member is selected to remove a first piece of debris, the second end member is selected to remove a second piece of debris, and the first piece of debris is larger than the second piece of debris.

16. The method of claim 14, wherein each of the elongated member, the first end member, and the second end member is made from one or more of: paper, biodegradable plastic, wood, bamboo, wire, polyester, rayon fibers, cotton fibers, polyurethane, resins, and natural rubbers, and
wherein the covering layer comprises one or more of rayon fiber, cotton fiber, polyester fiber, medical grade adhesive, and mixture thereof.

* * * * *